US006018029A

United States Patent [19]
Fuller et al.

[11] Patent Number: 6,018,029
[45] Date of Patent: Jan. 25, 2000

[54] DNA ENCODING CANINE INTERLEUKIN-1 RECEPTOR ANTAGONIST

[75] Inventors: Gerald Maxwell Fuller, Birmingham; Nelson Luis Fuentes, Bham, both of Ala.

[73] Assignee: UAB Research Foundation, Birmingham, Ala.

[21] Appl. No.: 09/000,630

[22] Filed: Dec. 30, 1997

Related U.S. Application Data

[62] Division of application No. 08/862,730, May 23, 1997.

[51] Int. Cl.[7] .................................................. C07K 14/54
[52] U.S. Cl. ........................... 530/351; 530/350; 424/85.2
[58] Field of Search .................................. 530/350, 351; 424/85.2

[56] References Cited

U.S. PATENT DOCUMENTS

| | | |
|---|---|---|
| Re. 35,450 | 2/1997 | Dower et al. . |
| 4,894,333 | 1/1990 | Cerretti et al. . |
| 4,902,708 | 2/1990 | Kim . |
| 4,968,607 | 11/1990 | Dower et al. . |
| 4,975,464 | 12/1990 | Imaki et al. . |
| 5,075,222 | 12/1991 | Hannum et al. . |
| 5,081,228 | 1/1992 | Dower et al. . |
| 5,180,812 | 1/1993 | Dower et al. . |
| 5,196,402 | 3/1993 | Braganza et al. . |
| 5,220,018 | 6/1993 | Bock et al. . |
| 5,286,739 | 2/1994 | Kilbourn et al. . |
| 5,286,847 | 2/1994 | Gehrke et al. . |
| 5,296,592 | 3/1994 | Dower et al. . |
| 5,319,071 | 6/1994 | Dower et al. . |
| 5,334,380 | 8/1994 | Kilbourn et al. . |
| 5,350,683 | 9/1994 | Sims et al. . |
| 5,455,330 | 10/1995 | Haskill et al. . |
| 5,464,937 | 11/1995 | Sims et al. . |
| 5,488,032 | 1/1996 | Dower et al. . |
| 5,492,888 | 2/1996 | Dower et al. . |
| 5,508,262 | 4/1996 | Norman . |
| 5,552,536 | 9/1996 | Nicholson et al. . |
| 5,563,046 | 10/1996 | Mascarenhas et al. . |

OTHER PUBLICATIONS

Pickvance, et al., "Immunolocalization of selected cytokines and proteases in canine articular cartilage after transarticular loading," *J. of Ortho. Res.,* 1993; 11(3):313–3223.

Shuster, et al., "Administration of recombinant human interleukin 1 receptor antagonist during endotoxin–induced mastitis in cows," *American Journal of Veterinary Research,* 1995; 56:313–320.

Waage and Espevik, "Interleukin 1 Potentiates the Lethal Effect of Tumor Necrosis Factor α/Cachectin in Mice," *J. Exp. Med.,* 1988; 167:1987–1992.

Wakabayashi, et al., "A specific receptor antagonist for interleukin 1 prevents *Escherichia coli*–induced shock in rabbits," *The FASEB Journal,* 1991; 5:338–343.

Zahedi, et al., "The mouse interleukin 1 receptor antagonist protein: Gene structure and regulation in vitro," *Cytokine* 1994; 6:1–9.

Aiura, et al., "Interleukin–1 (IL–1) Receptor Antagonist Prevents *Staphylococcus epidermidis*–Induced Hypotension and Reduces Circulating Levels of Tumor Necrosis Factor and IL–1β in Rabbits," *Infection and Immunity,* Aug. 1993, pp. 3342–3350.

Benton and Davis, "Screening gt Recombinant Clones by Hybridization to Single Plaques in situ," *Science,* Apr. 1977, pp. 180–182.

Bilgen, et al., "Attempts to Reduce Post–Transplant Pancreatitis in Rats and Dogs with the Somatostatin Analogue SMS 201–995," *Trans. Proc.,* 1989; 21(1):2829–2830.

Caron et al., "Chondroprotective effect of intraarticular injections of interleukin–1 receptor antagonist in experimental osteoarthritis. Supression of collagenase–1 expression," *Arthritis and Rheumatism,* 1996; 39:1535–1544.

Carter, et al. "Purification, cloning, expression and biological characterization of an interleukin–1 receptor antagonist," *Nature,* 1990; 344:633–638.

Cominelli, et al., "Rabbit Interleukin–1 Receptor Antagonist,". *J. of Biol. Chem.,* 1994; 269:6962–6971.

Dinarello, et al., Interleukin–1 and Interleukin–1 Receptor Antagonist., *Nutrition,* 1995; 11:492–494.

Dinarello, et al., "Interleukin–1 and Interleukin–1 Antagonism," *Blood,* 1991; 77:1627–1643.

Eisenberg, et al., "Primary structure and functional expression from complementary DNA of a human interleukin–1 receptor antagonist," *Nature,* 1990; 343:341–346.

Eisenberg, et al., "Interleukin 1 receptor antagonist is a member of the interleukin 1 gene family: Evolution of a cytokine control mechanism," *Immunology,* 1991; 88:5232–5236.

Evans, et al., "Progress toward the Treatment of Arthritis by Gene Therapy," *Annals of Medicine,* 1995; 27:543–546.

Fernandes, et al., "Effects of tenidap on the progression of osteoarthritic lesions in a canine experimental model.Supresion of metalloprotease and interleukin–1 activity," *Arthritis ans Rheumatism,* 1997; 40:284–294.

Fischer, et al., Comparision between effects of interleukin–1 administration and sublethal endotoxemia in primates, *the American Physiological Society,* 1991:R442–R452.

Fischer, et al., "Interleukin–1 Receptor Blockade Improves Survival and Hemodynamic Performance in *Escherichia coli* Septic Shock, but Fails to Alter Host Responses to Sublethal Endotoxemia," *J. Clin. Invest.,* 1992 89:1551–1557.

Goto, et al., "Interleukin–1 receptor antagonist in inflammatory exudate cells of rabbits. Production, purification and determination of primary structure," *Immunology* 1992; 77: 235–244.

Charles A. Dinarello, M.D., Supplement to Nutrition, 1995, vol. 11, No. 5: 492–497.

OTHER PUBLICATIONS

*Primary Examiner*—Garbette D. Draper
*Attorney, Agent, or Firm*—Rebecca J. Kaufman; Bruce D. Gray; Kilpatrick Stockton LLP

[57] ABSTRACT

Canine IL-1 receptor antagonist protein, DNAs, and expression vectors carrying DNA sequence encoding canine IL-1 receptor antagonist are disclosed.

1 Claim, 5 Drawing Sheets

OTHER PUBLICATIONS

C. H. Evans and P. D. Robbins, Annals of Medicine, 1995, 27:543–546.

J. Lewthwait, Journal of Rheumatology, Mar. 21(3):467–72.

Fabio Cominelli, The Journal of Biological Chemistry, Mar. 4, 1994, vol. 269, pp. 6962–6971.

GL Hung, Gene Therapy, Jan., 1994, 1(1):64–9.

Kamyar A. Zahedi, Cytokine, Jan., 1994, vol. 6, No. 1, pp. 1–9.

Koichhi Aiura, Infection and Immunity, Aug., 1993, vol. 61, No. 8, pp. 3342–3350.

J. Martel–Pelletier, Biochimica et Biophsica Acta., Feb. 17, 1993, 1175(3):302–305.

James A. Lederer, Journal of Leukocyte Biology, Jun., 1992, vol. 51, pp. 586–590.

Eva Fischer, Journal of Clinical Investigation, May, 1992, vol. 89, pp. 1551–1557.

F. Goto, Immunology, 1992, vol. 77, pp. 235–244.

Andrew Lennard, Cytokine, Mar., 1992, vol. 4, No. 2, pp. 83–89.

Hitoshi Matsuchime, Blood, Aug. 1, 1991, vol. 78, No. 3, pp. 616–623.

Charles A. Dinarello, Blood, Apr. 15, 1991, vol. 77, No. 8, pp. 1627–1652.

Go Wakabayashi, The FASEB Journal, Mar., 1991, vol. 5, pp. 338–343.

S. P. Eisenberg, Proc. Natl. Acad. Sci. USA, Jun., 1991, Immunology, vol. 88, pp. 5232–5236.

Kjell Ohlsson, Nature, Dec. 6, 1990, vol. 348, pp. 550–552.

D. B. Carter, Nature, Apr. 12, 1990, vol. 344, pp. 633–638.

Stephen B. Eisenberg, Nature, Jan. 25, 1990, vol. 343, pp. 341–346.

E. J. Sillenaar Bilgen, Transplantation Proceedings, Feb., 1989, vol. 21, No. 1, pp. 2829–2830.

C. Natanson, Journal of clinical Investigation, Jan., 1989, 83(1):243–251.

Seijiro Okusawa, Journal of Clinical Investigation, Apr., 1988, vol. 81, pp. 1162–1172.

Anders Waage, Journal of Experimental Medicine, Jun., 1988, vol. 167, pp. 1987–1992.

H. Okayama, Molecular & Cellular Biology, Feb., 1983, 3(2):280–289.

W. David Benton, Science, vol. 196, Apr. 8, 1977, pp. 180–182.

Granowitz, et al., "Pharmacokinetics, Safety and Immunomodulatory Effects of Human Recombinant Interleukin–1 Receptor Antagonist in Healthy Humans," *Cytokine*, 1992 4(5):353–360.

Haskill, et al., "cDNA Cloning of an Intracellular Form of the Human Interleukin 1 Receptor Antagonist Associated with Epithelium," *Proc. Natl. Acad. Sci. USA,* 1991 88(9):3681–5.

Houssiau, "Cytokines in rheumatoid arthritis," *Clinical Rheumatology,* 1995 14 Suppl. 2:10–3.

Hung, et al., "Suppression of intra–articular responses to interleukin–1 by transfer of the interleukin–1 receptor antagonist gene to synovium," *Gene Therapy* 1994; 1:64–69.

Lebedenko and Berlin, "PCR–Mediated Synthesis of a Gene Coding for the Interleukin 1 Receptor Antagonist," *Bioorg. Khim.,* 19(5): 586–8 (1993).

Lederer and Czuprynski, "Characterization and identification of interleukin 1 receptors on bovine neutrophils," *Journal of Leukocyte Biology* 1992; 51:586–590.

Lennard, et al., "Cloning and Chromosome Mapping of the Human Interleukin–1 Receptor Antagonist Gene," *Cytokine* 1992; 4:83–89.

Lewthwaite, et al., "The effect of recombinant human interleukin 1 receptor antagonist on the induction phase of antigen induced arthritis in the rabbit," *Journal of Rheumatology* 1994; 21:467–472.

Martel–Pelletier, et al., "The synthesis of IL–1 receptor antagonist (IL–1ra) by synovial fibroblasts in markedly increased by the cytokines TNF–alpha and IL–1," *Biochimica et Biophysica Acta.* 1993; 1175(3)302–5.

Matsushime, et al., "Cloning and Expression of Murine Interleukin–1 Receptor Antagonist in Macrophages Stimulated by Colony–Stimulating Factor 1," *Blood* 1991; 78:616–623.

Natanson, et al., "Role of endotoxemia in cardiovascular dysfunction and mortality. *Escherichia coli* and *Staphylococcus aureus* challenges in a canine model of human septic shock," *Jour. of Clin. Invest.* 1989; 83(1):243–251.

Ohlsson, et al., "Interleukin–1 receptor antagonist reduces mortality from endotoxin shock," *Nature* 1990; 348:550–552.

Okayama, et al., "A cDNA cloning vector that permits expression of cDNA inserts in mammalian cells," *Molecular and Cellular Biology* 1983; 3:280–289.

Okusawa, et al., "Interleukin 1 Induces a Shock–like State in Rabbits," *J. Clin. Invest.* 1988; 81:1162–1172.

Lebedinko et al Bioorg Khim 1993, 19(5) pp. 586–588.

Haskill et al *PNAS* 1991 88 (9) pp. 3681–3685.

Fig 1.

```
ACGGCTGCGA GAAGACGACA GAAGGGGGCA GTGTCCCGTT GCCTCGCTGT GGCCACCGAA   60

TGGAAACCTG CAGGTGTCCT CTCAGCTACC TAATCTCTTT CCTCCTTTTC CTGCCCCATT  120
                              Seq 18
CAGAGACAGC CTGCCGTCCC TTGGGGAAGA GACCTTGCAG GATGCAAGCC TTCAGAATCT  180
     Seq 12
GGGATGTTAA CCAGAAGACC TTCTACCTGA GGAATAACCA ACTAGTCGCT GGATACTTGC  240

AAGGATCAAA TACTAAATTA GAAGAGAAGT TAGATGTGGT GCCCGTCGAG CCTCATGCCG  300

TGTTCTTGGG GATCCATGGG GGGAAGCTGT GCCTGGCCTG TGTCAAGTCT GGAGATGAGA  360
      Seq 16
CCAGGCTCCA GCTGGAGGCC GTTAACATCA CTGACCTGAG TAAGAACAAG GATCAAGACA  420
                            Seq 14
AGCGCTTTAC CTTCATCCTC TCAGACAGTG GCCCCACCAC CAGCTTTGAG TCTGCTGCCT  480
                                          Seq 17
GCCCTGGCTG GTTCCTCTGC ACAGCACTGG AGGCCGACCG GCCTGTCAGC CTCACCAACA  540
                                                  Seq 19
GACCAGAAGA GGCCATGATG GTCACTAAGT TCTACTTCCA GAAGGAATAA TAGTGTGTCC  600
       GAA
ATTCCGTGCT TCCCCCCCAC TCCCAACACA TCAATGACTC CAGAGATGCC TCTCCATTCT  660
                                                  Seq 10
GCCTGGGGTC TCCTGGCTGT GGTGGAGGCT CTGAGGAGCA GCCTCGGTGG GGTGGACCCT  720

CAGAAGGATG TATGAGAGCC CTGGTAACGG GACCCTGCCT CCAGCCTCCT CAGCTAGCCA  780

ACCTCAATGC TGCCACCACA GTGGTCTTTC TAAAGTGCAC CTCTAGCTGC AGCACTGCTC  840

CAGGCCTTTC AGGGCTGCCT CTGCCTTCTG GATTAAAGCC AGGCTGCTTG GCCAGCCTGG  900

CCCCCTGCTC TCCTCTCCGT AACTCCTTGC TCTCCTCCCT TGCCCCATGT CCATGTCCTG  960

GATCCCTCCT GCCCCTTTGC TGGCCTCCCA AACCTTGTGT TTTGCAAACC GATGCTGTTC 1020

TGTGGGGAAA CCTTAGAGTC TGTGCCAAGA TGGCCGCTAA GGATTTCAAC TTGGCTTTCC 1080

TTTGAAGCCA ATTTCATCCA GTTTCAAGGG AGAGTCCTTT ATTTAGACAC TATGTCCATT 1140

CTGGAAANGT GTGGGCAAGG ATGAAAAGTA GCTCTCCCTT TTGATTTCTC TTATTTTTGA 1200

ACGTCCTGAC CTGCAAAAAT GACAAGTTAG TGTGTTATGT TGGTCTCTAC TTTTTTTCTT 1260

TCTGTGATGT TCCTAAAGCC TGGCCCCACT GCTCCAGCGA GGTACCATTT CCACTCCAGG 1320
                              Seq 11
CCTTTGACAG CCACCTGCAG TGCTTGTCCT CCCCATCTCT CCCATCAAAA CTCCCAGCTG 1380

CAGGCCAGGG CATCAATGTG GCTCCACTGT TCCTGGGAGG GAGGAATTAC TCTCGGACCA 1440

TTTTACACTT CTGACACTCT GAGACTTGTT TGAAAGGTTG TGTCTCTGTC TGTCTCCCAC 1500

ACCAGACTGT GAGTTCCCAA GAGAAGGGAG CATGACCTCT GTGTTTTGGG GCTCCCGCAG 1560
                                                 Seq 13
GGCTGAGCAC ACAGCTCCGG CCCTTAGCAC GTGCTCACTG AATGTGTGTT GTATGTGTTG 1620

AGTAGAAAGG TTTTTACTTT TTGTGAATTA AGGTTTGTTT TACAATAAAA TTTTAAAAAT 1680

TCAAAAAAAA AAAAAAAAAA AAAAAAAAA                                  1710
```

```
                                                                                                          MATURE N-TERMINUS
MOUSE   ATGGAAATCTGCTGGGAGACCTTACAGTCACTCACTCTCTCCTTCTCATCCTTCTGTTCATTCAGAGGAGCCTGC  CGCCCTTCTGGGAAAAGACCT
RAT     ATGGAAATCTCAGGGAGACCTTACAGTCACTCACTCTCTCTCCTTCTCATCCTTCTGTTCGTTCAGAGTCAGCTGCC  CACCCTGCTGGGAAAGACCCT
HUMAN   ATGGAAATCTCAGAGGCCTCCGAGTCACTCACTACTCTCTCCTCTCCTCCTG      TTCCATTCAGACACCATGC  CGACCCTCTGGAGAAATCA
CANINE  ATGGAAACCTGCAGGTGTCCCTCTCAGCTACTCACTCTCTTTCCTCCTCCTG      CCCCATTCAGAGACAGCCTGC  CGTCCCTTGGGAGAGAGACCTT
RABBIT  ATGAGACCCTCCAGGACCCCAGCCACCGACCTCAGTCAATCTCCCCGCCTCCTCCTG  TTCCATTCAGACAGCAGCCTGC  CGCCCTTCTGGGAAAGACCTT

101
        GCAAGATGCAAGCCTTCAG  AATCTGGGATACTAACCAGAAGACCTTTACTGGAGAAACCTCATTCCTCGGGTACTTACAAGACCAATATCAA
        GCAAGATGCAAGCCCTTCAG  AATCTGGGATACTAACCAGAAGACCTTTACTGGAGAAACCTCATTCCTCGGGTACTTACAAGACCAATATCAA
        GCAAGATGCAAGCCTTCAG   AATCTGGGATGTTAACCAGAAGACCTTCTACTGGAGAACACCAGTCCATTGCTCGGGTACTTACAAGACCAATACGAA
        GCAGGATGCAAGCCTTCAG   AATCTGGGATGTTAACCAGAAGACCTTCTATCTACCTGGAGGATGAATAACCAACTAGTTCCTCGATATGTCAAGGACCAATGTCAA
        GCAGGATGCAGGCCTTCAG   AATCTGGGATGTTAACCAGAAGACCTTCTACTGGAGAAGACCAACCAACTAGTGCCTCGATATGTCAAGGATCAAATACTAA
                        I2                                                                          GCAAGGCCCAATGCAA

201
        ACTAGAAG  AAAAGATAGACATGGTGCCTATTGACTTCAGTGTGTTCTGGGCATCCACGGGGGCAAGCTGTGCCCTGTCTTGTGCCAAGTCTCGAGAT
        ACTAGAAG  AAAAGATAGACATGGTGCCTATTGACTTGACTTGCCTATTGCCTATTGCGTGTTCTGGGCATCCACGGGGCCAAGCTGTGCCTGTCTTGTGCCAAGTCTCGAGAT
        TTTAGAAG  AAAGATAGATGTGGTACCCATTGAGCCTCATGCTCAGCCTCAGCCTCAGCCTCAGCCTTGAGCCTCAGCCTTGAGCCTCAGCCTTGTCCTGTCTGTCAAGTCTCGTGAT
        ATTAGAAG  AGAAGTTAGATGATGTGGTGTGTGTGTGCCCGTGCCCGCTCAGCCTCAGCCTCAGCCTTGAGCCTCAGCCTTGAGCCTCAGCCTTGTGCCTGTCTGTCAAGTCTCGAAT
        ATTAGAAG  AAAGGATAGATGTGGTGCGCCCTTGAGCCCGTGCCCCTTGAGCCTCAGCCTCAGCCTTGAGCCTCAGCCTTGAGCCTCAGCCTTGTGCCTGTCTGTCAAGTCTCGGGAT
                                                        I3
301     GATATCAAGCTCCAGCTGGAG  GAAGTTAACTCACTCACTGATCTGAGCAGCAAGAACAAAGAAGAAGAAGAAGAAGAACAAGCCGCTTTACTTCATCCGCTCGAGAAAGGCCCCA
        GACACCAGCTCCAGCTCCAGCTGGAG  GACACCAGCTCCAGCTCCAGCTGGAGAGGTTAACATCACTCACTGATGTTCCTGCAGATGTTCCTCGCACAACTAGAGGGCCTCGTGACCGTCCTGTGAGCCTCACAACACACCGGAAGAGCCCT
        GAGACCAGACTCCAGCTCCAGCTGGAG  GCAGTTAACATCACTCACTGACCTGAGCCGAGAACAGGAGAACAGGAGAACAAGCCGCTTCGCTTCACTTCATCCGCTCCAGAACAGGAGGCCTA
        GAGACCAGCTCCAGCTCCAGCTGGAG  GCAGTTAACATCACTCACTGACCTGAGCCGAGAACAGGAGAACAGGAGAACAAGCCGCTTCGCTTCACTTCATCCGCTCAGACAGTGCCCA
        AAGATGAAGCTCCATTGGAG  GCCGTTAACATCACTCACTGACCTGGGCAGAAGAACAAGGAGCAGGAGAACAAGGACGACAAGCCGCTTCACTTCACTTCATCCGCTCCAATAGTGCCTA

401     CCACCAGCTTTGAGTCAGCTCAGCTGCCTGTCCTGTCCAAGATGTTCCTCTGCACAACACTAGAGGCTGCTGTGACCGTCCTGTGAGCCTCACAACACACCGGAAGAGCCCT
        CCACCAGCTTCGAATCACTTGCCTGTCGCGCGCCTGTCCCAAGATGTTCCTCTGCCAAGATGTTCCTCTGCACAACACTAGAGGCTGCTGTGACCGTCCTGTGAGCCTCACAACACCACAAACAGAGCCCT
        CCACCAGTTTGAGTCTGCGCTGTCCCCGCGTTGTTCCTGCCGATGAAGCTGACCAGCCCGGTCAGCCTGCAGCCTGCCCCAATATCCTGACGAAGGT
        CCACCAGCTTTGAGTCTGCTGCCTGTCCTGCCCGTGTCCTGCCGATGAAGACTGAGTAAGAACAAGATCAAGACACTGAGGCCAGCCGGCTCAGCCTGCAGCCTGCCCCAACAGACCAGACCAGAGACCAT
        CCACCACCTTCGAGTCGCTGCCTCCTGCCTCCTGCCCCGGCTGTTTCTGTCCCTCCCCCCGGGCCCCTGCTGTCCTGCCCGATGAAGGCCCTGAGGCGCTGCAGCCTGCAGCCTGCCTGCCCCAACAGACCAGACCAGAGACTCCAT

501     TATAGTCACGAAGTTCTACTTCCAGGAAGACCAATAG         537
        TACAGTCACAAAGTTCTACTTCCAGGAAGACCAATAG         537
        CATGTCACCAAATTCTACTTCCAGGAGGACGAGTAG          534
        GATGTCACTAAGTTCTACTTCCAGGAAGGAATAATAG         534
        CGTGGTCACCAAGTTCTACTTCCAGGAGGAGACCAGTAG       534
```

| | | | |
|---|---|---|---|
| RAT | MEICRGPYSHLISLLLILLFRSESAGHPAGKRPCKMQAFRIWDTNQKTFYLRNNQLIA | GYLQGPNTKLEEKIDMVPIDFRNVFLGIHGGKLCLSCVKSGDDTKLQLEEVNITDLNK | NKEEDKRFTFIRSETGPTTSFESLACPGWFLCTTLEADHPVSLTNTPKEPCTVTKFYFQEDQ |
| MOUSE | MEICWGPYSHLISLLLILLLLFHSEAACRPSGKRPCKMQAFRIWDTNQKTFYLRNNQLIA | GYLQGPNIKLEEKIDMVPIDLHSVFLGIHGGKLCLSCAKSGDDIKLQLEEVNITDLSK | NKEEDKRFTFIRSEKGPTTSFESAACPGWFLCTTLEADRPVSLTNTPEEPLIVTKFYFQEDQ |
| HUMAN | MEICRGLRSHLITLLLF LFHSETICRPSGRKSSKMQAFRIWDVNQKTFYLRNNQLVA | GYLQGPNVLEEKIDVVPIEPHALFLGIHGGKMCLSCVKSGDETRLQLEAVNITDLSE | NRKQDKRFAFIRSDSGPTTSFESAACPGWFLCTAMEADQPVSLTNMPDEGVMVTKFYFQEDE |
| RABBIT | MRPSRSTRRHLISLLLF LFHSETACRPSGKRPCRMQAFRIWDVNQKTFYLRNNQLVA | GYLQGPNAKLEERIDVVPLEPQLLFLGIQRGKLCLSCVKSGDKMKLHLEAVNITDLGK | NKEQDKRFTFIRSNSGPTTTFESASCPGWFLCTALEADQPVSLTNTPDDSIVVTKFYFQEDQ |
| CANINE | METCRCPLSYLISFLLF LPHSETACRPLGKRPCRMQAFRIWDVNQKTFYLRNNQLVA | GYLQGSNTKLEEKLDVVPVEPHAVFLGIHGGKLCLACVKSGDETRLQLEAVNITDLSK | NKDQDKRFTFILSDSGPTTSFESAACPGWFLCTALEADRPVSLTNRPEEAMMVTKFYFQKE |

DNA ENCODING CANINE INTERLEUKIN-1 RECEPTOR ANTAGONIST

CROSS REFERENCE TO OTHER APPLICATIONS

This is a division of pending patent application Ser. No. 08/862,730 filed on May 23, 1997.

FIELD OF THE INVENTION

The present invention relates generally to cytokine receptor antagonists, and specifically, to cDNA encoding the Interleukin-1 receptor antagonist (IL-1ra) for canine species.

BACKGROUND OF THE INVENTION

Interleukin-1 (IL-1) type cytokines and their respective receptors have been studied with much interest over the past ten years. Additionally, other molecular entities which have effect on or in association with the IL-1 cytokines and receptors have also drawn much interest. One such molecule has been a protein receptor antagonist now termed Interleukin-1 receptor antagonist (IL-1ra).

IL-1B is known to be a cytokine that triggers inflammatory processes (Dinarello C A, *Interleukin-1 and Interleukin-1 Antagonism*. Blood 1991; 77: 1627–1652) The action of the receptor antagonist, IL-1ra, presently appears to generate its effect by competitively blocking the ligand (IL-1) for the receptor (Dinarello C A, *Interleukin-1 and Interleukin-1 Receptor Antagonist*. Nutrition 1995; 11: 492–494). Studies have indicated that IL-1ra may have important implications for use as a therapeutic agent in the treatment against inflammatory diseases including endotoxin-*induced shock, pancreatitis, mastitis, and rheumatoid arthritis (Ohlsson K, Bjork P, Bergenfeldt M, Hageman R, and Thompson R, Interleukin-1 receptor antagonist reduces mortality from endotoxin shock*. Nature 1990; 348: 550–552; U.S. Pat. No. 5,508,262 by Norman J G, *Interleukin-1 receptor antagonist decreases severity of acute pancreatitis*, 1996, University of South Florida, Tampa, Fla.: U.S.A.; Shuster D and Kehrli M, *Administration of recombinant human interleukin 1 receptor antagonist during endotoxin-induced mastitis in cows*. American Journal of Veterinary Research 1995; 56: 313–320; Evans C H and Robbins P D, *Progress toward the Treatment of Arthritis by Gene Therapy*. Annals of Medicine 1995; 27: 543–546). Such therapeutic administration has been contemplated using the protein or its antibody via several regimens including oral, intravenous, intraperitoneal, intranasal, and subcutaneous administration. Where arthritic conditions are contemplated, direct injection into the joints is contemplated to directly administer the protein to the disease site where the ligand appears to migrate and induce the inflammatory response of the arthritic condition. Intra-synovial expression of human IL-1ra in rabbits is protective against injection of human IL-1, however, use of human IL-1ra does not protect against rabbit IL-1 induced arthritis in rabbits (Hung G, Galea-Lauri J, Mueller G, Georgescu H, Larkin L, Suchanek M, Tindal M, Robbins P, and Evans C, *Suppression of intra-articular responses to interleukin-1 by transfer of the interleukin-1 receptor antagonist gene to synovium*. Gene Therapy 1994; 1: 64–69; Lewthwaite J, Blake S, Hardingham T, Warden P, and Henderson B, *The effect of recombinant human interleukin 1 receptor antagonist on the induction phase of antigen induced arthritis in the rabbit*. Journal of Rheumatology 1994; 21: 467–472). Human IL-1ra has been tried in bovine to reduce the inflammation of mammary gland (Shuster D and Kehrli M, *Administration of recombinant human interleukin 1 receptor antagonist during endotoxin-induced mastitis in cows*. American Journal of Veterinary Research 1995; 56: 313–320). However, although IL-1 bioactivity in milk was prevented, no effect of using human IL-1ra was shown in the bovine model. Moreover, human IL-1ra does not bind to bovine neutrophil IL-1 receptor (Lederer J and Czuprynski C, *Characterization and identification of interleukin 1 receptors on bovine neutrophils*. Journal of Leukocyte Biology 1992; 51: 586–590). Therefore, there is a direct indication in the art for a need to obtain species specific receptor antagonists for use against various disease states in which use of receptor antagonist is indicated to be useful in treatment of such disease states.

The IL-1ra gene sequence has been identified in several species. Protein and/or DNA sequence has been disclosed for, human, mouse, rabbit, and rat (Eisenberg S P, Evans R, Arend W, Verderber E, Brewer M, Hannum C, and Thompson R C, *Primary structure and functional expression from complementary DNA of a human interleukin-1 receptor antagonist*. Nature 1990; 343: 341–346; Carter D B, Deibel M R, Dunn C J, Tomich C-S, Laborde A L, Slightom J L, Berger A E, Bienkowski M J, Sun F F, McEwan R N, Harris K W, Yem A W, Waszak G A, Chosay J G, Sieu L C, Hardee M M, Zurcher-Neely H A, Reardon I M, Heinrikson R, Truesdell S, Shelly J, Eessalu T, Taylor B, and Tracey D, *Purification, cloning, expression and biological characterization of an interleukin-1 receptor antagonist*. Nature 1990; 344 : 633–638; Lennard A, Gorman P, Carrier M, Griffiths S, Scotney H, Sheer D, and Solari R, *Cloning and Chromosome Mapping of the Human Interleukin-1 Receptor Antagonist Gene*. Cytokine 1992; 4: 83–89; Matsushime H, Roussel M, Kouji M, Hishinuma A, and Sherr C, *Cloning and Expression of Murine Interleukin-1 Receptor Antagonist in Macrophages Stimulated by Colony-Stimulating Factor 1*. Blood 1991; 78 : 616–623; Zahedi K, Uhlar C, Rits M, Prada A, and Whitehead A, *The mouse interleukin 1 receptor antagonist protein: Gene structure and regulation in vitro*. Cytokine 1994; 6: 1–9; Goto F, Goto K, Miyata T, Ohkawara S, Takao T, Furukawa S, Maeda T, Iwanaga S, Shimonishi Y, and Yoshinaga M, *Interleukin-1 receptor antagonist in inflammatory exudate cells of rabbits. Production, purification and determination of primary structure*. Immunology 1992; 77 : 235–244; Cominelli F, Bortolami M, Pizarro T, Monsacchi L, Ferretti M, Brewer M, Eisenberg S; and Ng R, *Rabbit Interleukin-1 Receptor Antagonist*. J. of Biol. Chem. 1994; 269 : 6962–6971). The protein sequences of the known species are very similar as noted in FIG. 4. As shown the Table I, the highest percent homology is between rat and mouse at 90% and the lowest homology is between human and rat at 75%. In the table, D=dog, H=human, M=mouse, RB=rabbit, and R=rat.

TABLE I

|    | R   | M   | H   | D   | RB  |
|----|-----|-----|-----|-----|-----|
| R  | 100 |     |     |     |     |
| M  | 90  | 100 |     |     |     |
| R  | 75  | 77  | 100 |     |     |
| D  | 74  | 74  | 80  | 100 |     |
| RB | 78  | 79  | 78  | 76  | 100 |

Thus, as indicated from the homologies, it is likely that species specific binding may be necessary for the canine IL-1ra protein to interact with its respective receptor molecule(s) to provide effective treatment for such clinical indications as IL-1 associated arthritis. As is typically the case concerning ligand, receptor, and a receptor antagonist binding, the variation in amino acid sequence is very important to the specific binding characteristics. Moreover, in a long-term treatment, small differences between the same protein in different species may give rise to an immune response. One objective of the current invention is to alleviate the likelihood of an immune response by obtaining canine IL-1ra to be used specifically in dog species.

In studying the effect of IL-1ra in treatment of various disease states, including arthritic conditions, canine species have been recognized as an appropriate animal model (Caron J F, Fernandes J C, Martel-Pelletier J, Tardif G, Mineau F, Geng C, Pelletier J P, *Chondroprotective effect of intraarticular injections of interleukin-1 receptor antagonist in experimental osteoarthritis. Supression of collagenase-1 expression*. Arthritis and Rheumatism 1996; 39: 1535–1544; Picvance E O, Oegema T R, Thompson R C, *Immunolocalization of selected cytokines and proteases in canine articular cartilage after transarticular loading*. Journal of Orthopaedic Research 1993; 11: 313–323; Fernandes J C, Caron J P, Martel-Pelletier J, Jonanovic D, Mineau F, Tardif G, Otterness I G, Pelletier J P, *Effects of tenidap on the progression of osteoarthritic lesions in a canine experimental model. Suppression of metalloprotease and interleukin-1 activity*, Arthritis and Rheumatism 1997; 40: 284–294). Moreover, many breeds of dog are susceptible to arthritic disease and can benefit directly from advances in the art to treat canine arthritic conditions. The current invention advances such art through obtaining canine IL-1ra DNA sequence from which the protein may be produced for use in treatment of canine diseases including arthritis.

SUMMARY OF THE INVENTION

The present invention provides isolated natural gene sequence encoding canine IL-1ra. The invention also provides isolated canine IL-1ra protein. A further embodiment of the present invention provides for DNA sequences encoding IL-1ra, in particular, canine IL-1ra selected from the group consisting of (a) a cDNA clone having a nucleotide sequence encoding an amino acid sequence of amino acids –25 through 151 of SEQ ID NO.:1; (b) a DNA capable of hybridization to a clone of (a) under moderately stringent conditions and which encodes a biologically active canine IL-1ra molecule; and (c) a DNA having a sequence which is degenerate as a result of the genetic code to a DNA as defined in (a) or (b) above and which encodes biologically active canine IL-1ra molecules.

Another preferred embodiment of the invention contemplates recombinant expression vectors having the DNA sequences described above as well as the IL-1ra proteins encoded therein and expressed by the expression vectors and the processes of producing said proteins from said vectors. Yet another embodiment of the invention contemplates the purification of said proteins.

Still other objects of the invention include treating dogs susceptible to arthritic conditions by administration of an effective amount of the canine IL-1ra protein or the DNA by gene therapy.

BRIEF DESCRIPTION OF THE DRAWINGS

FIG. 1 is a single stranded nucleotide sequence depicting the cDNA retrieved from reverse transcription of canine mRNA encoding IL-1ra. The figure also depicts the locations of primers and direction of sequencing used to obtain the DNA sequence as well as to clone the cDNA into an expression vector. The sequence depicted is the same as SEQ ID NO 1.

FIG. 3 is a comparison of the DNA sequence of canine IL-1ra with that of the rat, mouse, rabbit, and human. The sequences are depicted beginning at the 5' initiation codon ATG and terminating with the nonsense codon at the 3' end. Notations I1, I2, and I3 depict locations of introns in species in which the genomic DNA sequence has been obtained. The figure further notes the location of the primers used for creating a PCR generated human sequence probe for obtaining the canine cDNA. DNA sequences for rat, mouse, rabbit and human are listed in sequence listing SEQ ID NOs 24 to 27.

FIG. 4 is a comparison of the full length canine IL-1ra peptide sequence with that of human, mouse, rabbit, and rat. The figure is presented in one letter amino acid code for necessity of clarity. A=Ala, N=Asn, D=Asp, R=Arg, C=Cys, Q=Gln, E=Glu, G=Gly, H=His, I=Ile, L=Leu, K=Lys, M=Met, F=Phe, P=Pro, S=Ser, T=Thr, W=Trp, Y=Tyr, V=Val. The sequences are listed in SEQ ID NOs 20 to 23.

DETAILED DESCRIPTION OF THE INVENTION

Figure 2:
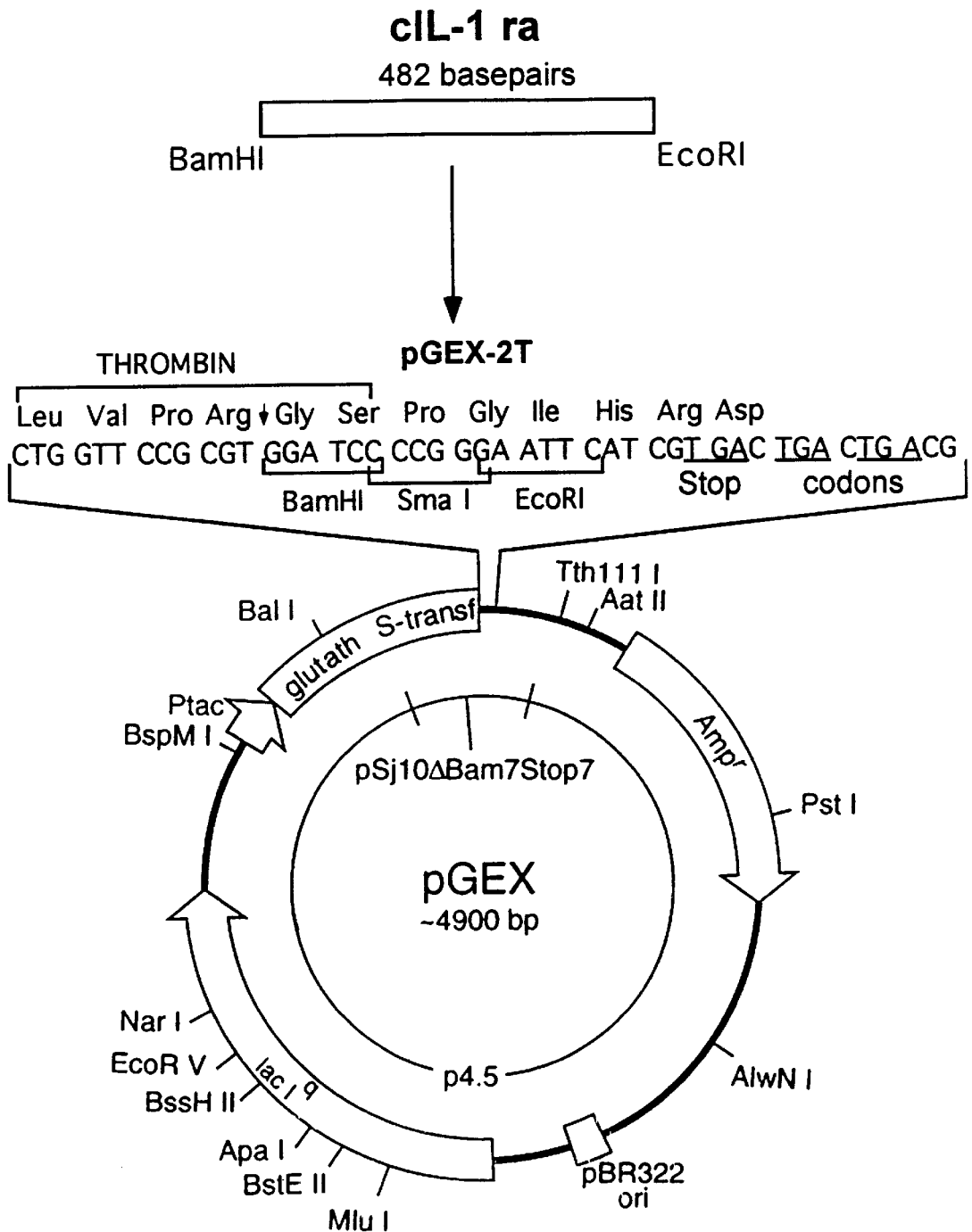
FIG. 2 represents a schematic diagram of the glutathione-S-transferase (GST) fusion protein expression construct plasmid pGEX-2T. The cDNA is inserted into the plasmid via the BamHI restriction site at the 5' and an EcoRI restriction site at the 3'.

Isolation and Identification of cDNA Sequence of canine IL-1ra

General Cloning Techniques

The materials and methods used to establish a cDNA library containing the cDNA sequence that encodes full length canine IL-1ra are well known in the recombinant DNA art. However, a general description of the materials and methods used in the current invention is presented for clarity.

Preferred embodiment for a canine cDNA library and screening thereof.

White blood cells were isolated from fresh dog blood by layering whole blood on an isotonic solution of Accudenz (Accurate Chemical New York) 60% in HBSS buffer. The white blood cells obtained after centrifugation were plated and incubated in RPMI media 10% FBS. After 2 hours incubation at 37° C., the media was gently aspirated. Fresh media was added and the remaining adherent macrophages were incubated overnight at 37° C., 5% $CO_2$.

Following overnight incubation, the cells were stimulated with LPS(20 ug/ml) in fresh media for 6 hours. RNA was extracted and purified utilizing standard guanidine thiocyanate/oligo (dT) priming protocol as described (Okayama H, Berg P, *A cDNA cloning vector that permits expression of cDNA inserts in mammalian cells*. Molecular and Cellular Biology 1983; 3: 280–289). An aliquot of the isolated oligo (dT) RNA was electrophoresed to examine the quality of the RNA. After determining the quality and quantity of the RNA, 20 ug was used to construct a cDNA library.

The cDNA library cloning materials utilized that of Clontech, (Palo Alto Calif.) to construct an oligo(dT) primed lambda gt11 library. The cDNA was blunt end ligated to adaptors which contained Eco RI restriction sites. The cDNA was then ligated to the lambda gt11 using Eco R1 restriction site through the adaptor. The library was screened according to standard techniques such as that described (Sambrook J F, Frisch E F, Maniatis T, *Molecular cloning, a Laboratory Manual*. Cold Spring Harbor Laboratory Press. Cold Spring Harbor. 1989) using as a hybridization probe human IL-1ra DNA sequence amplified by RT-PCR. The primer sequences used for creating the human probe are designated in the sequence listing by SEQ ID NO. 6 and SEQ ID NO 7. These sequences conform to the human IL-1ra beginning from the mature protein codon for the 5' probe of SEQ ID NO 6 and beginning from the termination codon at the 5' end of SEQ ID NO 7.

The largest clone (designated c IL-1ra) as determined by agarose gel was 1.7 kb. This clone was subcloned into M13 mp18 vector via the Eco R1 restriction site and DNA sequence analysis was carried out using the Perkin-Elmer Applied Biosystem 377 Sequencer. Oligonucleotides used as sequencing primers and described in SEQ ID Nos. 8 to 17 were synthesized by Integrated DNA Technologies (Coralville, Iowa). Sequence data were analyzed using the University of Wisconsin Genetic Computer Group Program on a VAX DCL computer.

Analysis of the cDNA IL-1ra Clones

The cDNA obtained for full length canine IL-1ra contains 1710 nucleotides and one open reading frame with 528 nucleotides. The polyadenylation signal is 1071 bases 3' to the stop codon and 13 base upstream of the poly (A) tail. The open reading frame (ORF) is preceded by 59 nucleotides of untranslated region (UTR) and is followed by a 3' UTR of 1092 nucleotides excluding the poly(A)tail.

The intron organization is believed to be similar to those found in human, mouse, rat and rabbit IL-1ra genes (Cominelli F, Bortolami M, Pizarro T, Monsacchi L, Ferretti M, Brewer M, Eisenberg S, and Ng R, *Rabbit Interleukin-1 Receptor Antagonist*. J. of Biol. Chem. 1994; 269 : 6962–6971; Eisenberg S, Brewer M, Verderber E, Heimdal P, Brandhuber B, and Thompson R, *Interleukin 1 receptor antagonist is a member of the interleukin 1 gene family: Evolution of a cytokine control mechanism,*. Immunology 1991; 88: 5232–5236) and described as a common organization to IL-1 family members (Zahedi K, Uhlar C, Rits M, Prada A, and Whitehead A, *The mouse interleukin 1 receptor antagonist protein: Gene structure and regulation in vitro*. Cytokine 1994; 6: 1–9). The coding region sequence has 84% identity with the human IL-1ra sequence of the same region. The short 5' untranslated region has 58% similarity and the 3' UTR has 62% of similarity as compared to the human homologous.

The predicted amino acid sequence encoded by the canine IL-1ra gene is very similar to the sequences of the species above mentioned having 80% identity to the human protein. Thus, the receptor antagonist family demonstrates a very high level of conservation between these sequences. The N-terminal 25 amino acids are tentatively identified as the signal peptide. The canine sequence is similar to the other species in that the sequence at the position of the purported mature protein start in the canine, beginning RPLGKR, parallels the other species having a mature protein sequence starts beginning RPSGKR (mouse and rabbit), RPSGRK (human) and HPAGKR (rat). A mature protein beginning at this position results in a molecule having 151 amino acid residues and a predicted molecular weight of 16,610 KD.

Expression of Canine IL-1ra Protein

Figure 5:
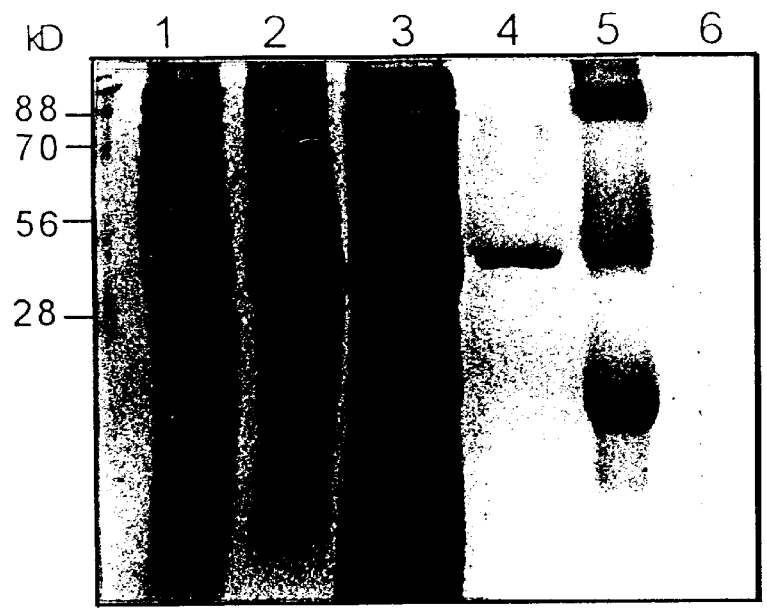
FIG. 5 is a PAGE gel showing expression of fusion peptide containing IL-1ra and the purified fusion protein expression product as well as the fusion product digested with thrombin.

The cDNA clone c IL-1ra was amplified by PCR using primers designated in SEQ ID Nos. 18 and 19. These primers were designed to generate a 5' Bgl II restriction site for use in cloning the gene into the Bam HI site of the GST fusion protein expression vector pGEX-2T (Pharmacia), and a 3' EcoRI restriction site located downstream of the termination codon for cloning into the Eco RI site of the expression plasmid. The PCR product which was generated using these primers comprised a 495 base pair sequence of which (1) 456 base pairs encode the IL-1ra protein from the cystine at amino acid position 25 of the full length protein (nucleotide base 132), (2) the necessary amino acids glycine and serine 5' to the cystine for thrombin cleavage recognition, and (3) at the 3' end, natural sequence down stream of the termination codon into which an Eco RI restriction site had been engineered. The fusion protein construct was then expressed in *E. coli* strain DH5α- using IPTG induction methodology. FIG. 5 shows a 12% Coomassie brilliant blue stained SDS-PAGE of canine IL-1ra fusion and cleaved protein product. The IL-1ra may be specifically cleaved from the fusion protein using thrombin according to standard techniques. Lane 1 shows cells sonicated before induction with IPTG. Lane 2 shows supernatant of cells sonicated after induction with IPTG and cell cultured for 5 hours in LB Broth (shaker culture). Lane 3 depicts a pellet of sonicated cells post IPTG induction. Lane 4 shows the fusion protein after elution from glutathione-sepharose column separation. As is clear, the protein may be isolated to substantially high purity as a fusion protein product. Lane 5 depicts flow through of glutathione-sepharose column loaded with supernatant of sonicated cells post IPTG induction. Lane 6 shows flow through of glutathione sepharose column loaded with fusion protein digested with thrombin. The free IL-1ra generates a band just under 19 KD.

Purification of the IL-1ra Protein

Figure 6:
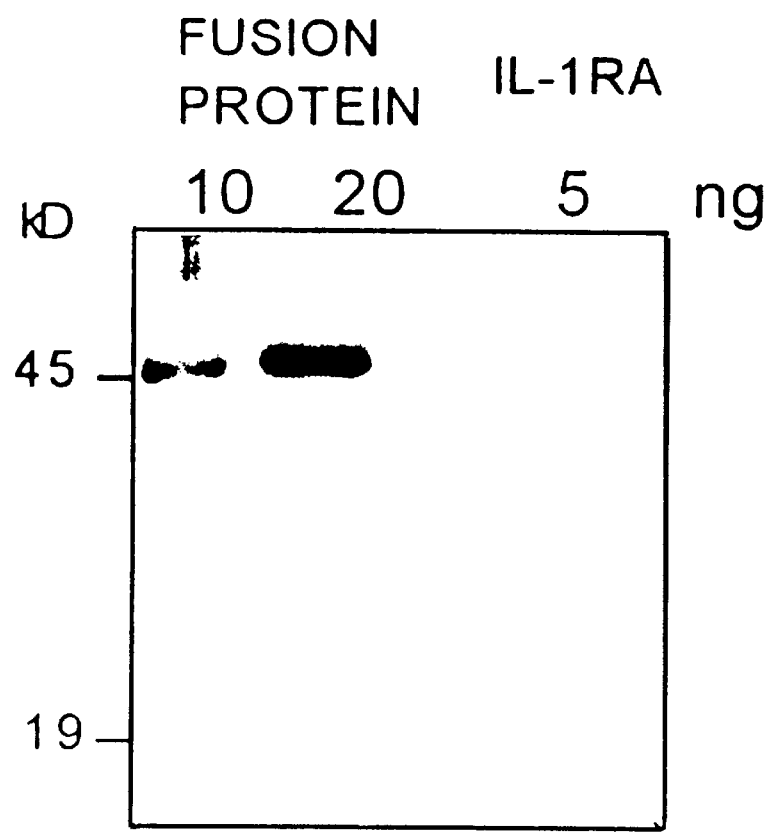
FIG. 6 is an western blot of both the purified IL-1ra fusion and cleaved proteins detected by an enhanced chemiluminescence (ECL) system.

The fusion protein was purified over a Glutathione-Sepharose column (1×10 cm). Following column separation, the IL-1ra portion was released by digestion of the fusion protein with human thrombin (1 mg/ml). As shown in FIG. 6 both the fusion protein and released IL-1ra were detected on SDS-PAGE western blot using chemiluminescence technique (Pierce Rockford, Ill.). The released protein may be obtained in highly pure form.

Antagonist Activity

The western blot methodology discussed above used goat anti-human IL-1ra antibody (R&D Systems Minneapolis, Minn.) and shows that canine IL-1ra amino acid sequence is very similar to the human protein having good immunological cross reactivity. Thus, one can expect likelihood that its metabolic activity in the dog may be similar to that of the human protein's activity in man.

In Vitro Test Blocking of IL-1 by Canine IL-1ra

Efficacy of the canine protein was tested indirectly by observation of its effect on the blocking of IL-6 mRNA induction in the THP-1 human monocyte cell line. It is well established that IL-1B induces the production of IL-6. Administration of IL-1B to these cells will induce IL-6 message. If IL-1B is blocked by administration of IL-1ra, then a drop in IL-6 message is observed as shown in table II (data in arbitrary units).

TABLE II

| Treatment of Cells | IL-6 message level |
|---|---|
| IL-1 | 12 |
| IL-1/IL-1ra | 4 |

Measurements of IL-6 mRNA were carried out by harvesting total RNA from treated cells followed by electrophoresis and Northern blot. The Northern blot was then exposed to a 32P labeled IL-6 specific PCR probe by standard hybridization techniques and the image of exposed film scanned for intensity in STORM 860 Phosphor screening system.

BRIEF DESCRIPTION OF THE SEQUENCE LISTING

SEQ ID NO:1 is a nucleotide sequence showing the cDNA sequence obtained for canine IL-1ra. The open reading frame (ORF) of the IL-1ra protein is defined by nucleotide base number 60 to base number 587. The predicted signal peptide sequence is defined by amino acids −25 to −1. The mature peptide is defined by amino acids 1–151.

SEQ ID NO: 2 is an amino acid sequence of the signal peptide of IL-1ra protein.

SEQ ID NO: 3 is an amino acid sequence of the mature IL-1ra protein.

SEQ ID NO: 4 is an amino acid sequence of the full length IL-1ra protein.

SEQ ID NO: 5 is an amino acid sequence of the fusion protein after cleavage with thrombin.

SEQ ID NO: 6–SEQ ID NO 7 are oligonucleotides used as human primers to construct the probe use for screening the dog cDNA library.

SEQ ID NO: 8–SEQ ID NO:17 are oligonucleotides used to sequence the full length canine cDNA. Sequences 8, 9, and 15 anneal to m13 and read downstream for number 8 and upstream for numbers 9 and 15. The locations for internal primers are shown on FIG. 1.

SEQ ID NO: 18–SEQ ID NO: 19 are oligonucleotides used to construct a mature canine IL-1ra gene sequence by polymerase chain reaction (PCR).

SEQ ID NO: 20–SEQ ID NO: 23 are three letter code amino acid sequences for human, mouse, rabbit, and rat IL-1ra.

SEQ ID NO: 24–SEQ ID NO: 27 are nucleotide sequences for human, mouse, rabbit and rat IL-1ra.

```
                        SEQUENCE LISTING (1) GENERAL INFORMATION:

(iii) NUMBER OF SEQUENCES: 27

(2) INFORMATION FOR SEQ ID NO:1:

(i) SEQUENCE CHARACTERISTICS:
        (A) LENGTH: 1710 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: N (iv) ANTI-SENSE: N (vi) ORIGINAL SOURCE:
        (A) ORGANISM: Canis familiaris
        (B) CELL TYPE: canine peripheral blood macrophage
        (C) CELL LINE: primary monocytes (vii) IMMEDIATE SOURCE:
        (A) LIBRARY: lambda gt11 cDNA
        (B) CLONE: Canine IL-1ra (ix) FEATURE:
        (A) NAME/KEY: CDS
        (B) LOCATION: 1 to 1710
        (C) OTHER INFORMATION:

(ix) FEATURE:
        (A) NAME/KEY: open reading frame
        (B) LOCATION: 60 to 587
        (C) OTHER INFORMATION:

(xi) SEQUENCE DESCRIPTION: SEQ ID NO:1:

ACGGCTGCGA GAAGACGACA GAAGGGGGCA GTGTCCCGTT GCCTCGCTGT                    50

GGCCACCGA ATG GAA ACC TGC AGG TGT CCT CTC AGC TAC CTA                    92
          Met Glu Thr Cys Arg Cys Pro Leu Ser Tyr Leu
          -25                 -20                 -15
```

```
ATC TCT TTC CTC CTT TTC CTG CCC CAT TCA GAG ACA GCC TGC          134
Ile Ser Phe Leu Leu Phe Leu Pro His Ser Glu Thr Ala Cys
            -10             -5                      -1

CGT CCC TTG GGG AAG AGA CCT TGC AGG ATG CAA GCC TTC AGA          176
Arg Pro Leu Gly Lys Arg Pro Cys Arg Met Gln Ala Phe Arg
1               5               10

ATC TGG GAT GTT AAC CAG AAG ACC TTC TAC CTG AGG AAT AAC          218
Ile Trp Asp Val Asn Gln Lys Thr Phe Tyr Leu Arg Asn Asn
15                  20                  25

CAA CTA GTC GCT GGA TAC TTG CAA GGA TCA AAT ACT AAA TTA          260
Gln Leu Val Ala Gly Tyr Leu Gln Gly Ser Asn Thr Lys Leu
    30                  35                  40

GAA GAG AAG TTA GAT GTG GTG CCC GTC GAG CCT CAT GCC GTG          302
Glu Glu Lys Leu Asp Val Val Pro Val Glu Pro His Ala Val
        45                  50                  55

TTC TTG GGG ATC CAT GGG GGG AAG CTG TGC CTG GCC TGT GTC          344
Phe Leu Gly Ile His Gly Gly Lys Leu Cys Leu Ala Cys Val
            60                  65                  70

AAG TCT GGA GAT GAG ACC AGG CTC CAG CTG GAG GCC GTT AAC          386
Lys Ser Gly Asp Glu Thr Arg Leu Gln Leu Glu Ala Val Asn
                75                  80

ATC ACT GAC CTG AGT AAG AAC AAG GAT CAA GAC AAG CGC TTT          428
Ile Thr Asp Leu Ser Lys Asn Lys Asp Gln Asp Lys Arg Phe
85                  90                  95

ACC TTC ATC CTC TCA GAC AGT GGC CCC ACC ACC AGC TTT GAG          470
Thr Phe Ile Leu Ser Asp Ser Gly Pro Thr Thr Ser Phe Glu
    100                 105                 110

TCT GCT GCC TGC CCT GGC TGG TTC CTC TGC ACA GCA CTG GAG          512
Ser Ala Ala Cys Pro Gly Trp Phe Leu Cys Thr Ala Leu Glu
        115                 120                 125

GCC GAC CGG CCT GTC AGC CTC ACC AAC AGA CCA GAA GAG GCC          554
Ala Asp Arg Pro Val Ser Leu Thr Asn Arg Pro Glu Glu Ala
            130                 135                 140

ATG ATG GTC ACT AAG TTC TAC TTC CAG AAG GAA TAA                  590
Met Met Val Thr Lys Phe Tyr Phe Gln Lys Glu
                145                 150 151

TAGTGTGTCC ATTCCGTGCT TCCCCCCCAC TCCCAACACA TCAATGACTC           640

CAGAGATGCC TCTCCATTCT GCCTGGGGTC TCCTGGCTGT GGTGGAGGCT           690

CTGAGGAGCA GCCTCGGTGG GGTGGACCCT CAGAAGGATG TATGAGAGCC           740

CTGGTAACGG GACCCTGCCT CCAGCCTCCT CAGCTAGCCA ACCTCAATGC           790

TGCCACCACA GTGGTCTTTC TAAAGTGCAC CTCTAGCTGC AGCACTGCTC           840

CAGGCCTTTC AGGGCTGCCT CTGCCTTCTG GATTAAAGCC AGGCTGCTTG           890

GCCAGCCTGG CCCCCTGCTC TCCTCTCCGT AACTCCTTGC TCTCCTCCCT           940

TGCCCCATGT CCATGTCCTG GATCCCTCCT GCCCCTTTGC TGGCCTCCCA           990

AACCTTGTGT TTTGCAAACC GATGCTGTTC TGTGGGAAA CCTTAGAGTC           1040

TGTGCCAAGA TGGCCGCTAA GGATTTCAAC TTGGCTTTCC TTTGAAGCCA          1090

ATTTCATCCA GTTTCAAGGG AGAGTCCTTT ATTTAGACAC TATGTCCATT          1140

CTGGAAAAGT GTGGGCAAGG ATGAAAAGTA GCTCTCCCTT TTGATTTCTC          1190

TTATTTTTGA ACGTCCTGAC CTGCAAAAAT GACAAGTTAG TGTGTTATGT          1240

TGGTCTCTAC TTTTTTTCTT TCTGTGATGT TCCTAAAGCC TGGCCCCACT          1290

GCTCCAGCGA GGTACCATTT CCACTCCAGG CCTTTGACAG CCACCTGCAG          1340

TGCTTGTCCT CCCCATCTCT CCCATCAAAA CTCCCAGCTG CAGGCCAGGG          1390
```

```
CATCAATGTG GCTCCACTGT TCCTGGGAGG GAGGAATTAC TCTCGGACCA        1440

TTTTACACTT CTGACACTCT GAGACTTGTT TGAAAGGTTG TGTCTCTGTC        1490

TGTCTCCCAC ACCAGACTGT GAGTTCCCAA GAGAAGGGAG CATGACCTCT        1540

GTGTTTTGGG GCTCCCGCAG GGCTGAGCAC ACAGCTCCGG CCCTTAGCAC        1590

GTGCTCACTG AATGTGTGTT GTATGTGTTG AGTAGAAAGG TTTTTACTTT        1640

TTGTGAATTA AGGTTTGTTT TACAATAAAA TTTTAAAAAT TCAAAAAAAA        1690

AAAAAAAAAA AAAAAAAAA                                         1710
```

(2) INFORMATION FOR SEQ ID NO:2:

(i) SEQUENCE CHARACTERISTICS:
       (A) LENGTH: 25 amino acids
       (B) TYPE: amino acid
       (D) TOPOLOGY: linear (ii) MOLECULE TYPE: signal peptide (xi) SEQUENCE DESCRIPTION: SEQ ID NO:2:

```
Met Glu Thr Cys Arg Cys Pro Leu Ser Tyr Leu
-25             -20             -15

Ile Ser Phe Leu Leu Phe Leu Pro His Ser Glu Thr Ala Cys
            -10             -5              -1
```

(2) INFORMATION FOR SEQ ID NO:3:

(i) SEQUENCE CHARACTERISTICS:
       (A) LENGTH: 151 amino acids
       (B) TYPE: amino acid
       (D) TOPOLOGY: linear (ii) MOLECULE TYPE: mature peptide (xi) SEQUENCE DESCRIPTION: SEQ ID NO:3:

```
Arg Pro Leu Gly Lys Arg Pro Cys Arg Met Gln Ala Phe Arg
1               5               10

Ile Trp Asp Val Asn Gln Lys Thr Phe Tyr Leu Arg Asn Asn
15              20              25

Gln Leu Val Ala Gly Tyr Leu Gln Gly Ser Asn Thr Lys Leu
        30              35              40

Glu Glu Lys Leu Asp Val Val Pro Val Glu Pro His Ala Val
            45              50              55

Phe Leu Gly Ile His Gly Gly Lys Leu Cys Leu Ala Cys Val
                60              65              70

Lys Ser Gly Asp Glu Thr Arg Leu Gln Leu Glu Ala Val Asn
            75              80

Ile Thr Asp Leu Ser Lys Asn Lys Asp Gln Asp Lys Arg Phe
85              90              95

Thr Phe Ile Leu Ser Asp Ser Gly Pro Thr Thr Ser Phe Glu
    100             105             110

Ser Ala Ala Cys Pro Gly Trp Phe Leu Cys Thr Ala Leu Glu
            115             120             125

Ala Asp Arg Pro Val Ser Leu Thr Asn Arg Pro Glu Glu Ala
            130             135             140

Met Met Val Thr Lys Phe Tyr Phe Gln Lys Glu
                145             150 151
```

(2) INFORMATION FOR SEQ ID NO:4:

(i) SEQUENCE CHARACTERISTICS:
    (A) LENGTH: 176 amino acids
    (B) TYPE: amino acid
    (D) TOPOLOGY: linear (ii) MOLECULE TYPE: IL-1ra full length peptide (xi) SEQUENCE DESCRIPTION: SEQ ID NO:4:

```
Met Glu Thr Cys Arg Cys Pro Leu Ser Tyr Leu
-25             -20                 -15

Ile Ser Phe Leu Leu Phe Leu Pro His Ser Glu Thr Ala Cys
            -10                 -5                   -1

Arg Pro Leu Gly Lys Arg Pro Cys Arg Met Gln Ala Phe Arg
1               5                   10

Ile Trp Asp Val Asn Gln Lys Thr Phe Tyr Leu Arg Asn Asn
15              20                  25

Gln Leu Val Ala Gly Tyr Leu Gln Gly Ser Asn Thr Lys Leu
        30              35                  40

Glu Glu Lys Leu Asp Val Val Pro Val Glu Pro His Ala Val
            45              50                  55

Phe Leu Gly Ile His Gly Gly Lys Leu Cys Leu Ala Cys Val
                60              65                  70

Lys Ser Gly Asp Glu Thr Arg Leu Gln Leu Glu Ala Val Asn
                75                  80

Ile Thr Asp Leu Ser Lys Asn Lys Asp Gln Asp Lys Arg Phe
85                  90                  95

Thr Phe Ile Leu Ser Asp Ser Gly Pro Thr Thr Ser Phe Glu
    100                 105                 110

Ser Ala Ala Cys Pro Gly Trp Phe Leu Cys Thr Ala Leu Glu
            115                 120                 125

Ala Asp Arg Pro Val Ser Leu Thr Asn Arg Pro Glu Glu Ala
                130                 135                 140

Met Met Val Thr Lys Phe Tyr Phe Gln Lys Glu
                145                 150 151
```

(2) INFORMATION FOR SEQ ID NO:5:

(i) SEQUENCE CHARACTERISTICS:
        (A) LENGTH: 154 amino acids
        (B) TYPE: amino acid
        (D) TOPOLOGY: linear (ii) MOLECULE TYPE: cleaved IL-1ra peptide from fusion construct (xi) SEQUENCE DESCRIPTION: SEQ ID NO:5:

```
Gly Ser Cys Arg Pro Leu Gly Lys Arg Pro Cys Arg Met Gln Ala
1               5                   10                  15

Phe Arg Ile Trp Asp Val Asn Gln Lys Thr Phe Tyr Leu Arg Asn
            20                  25                  30

Asn Gln Leu Val Ala Gly Tyr Leu Gln Gly Ser Asn Thr Lys Leu
                35                  40                  45

Glu Glu Lys Leu Asp Val Val Pro Val Glu Pro His Ala Val Phe
                50                  55                  60

Leu Gly Ile His Gly Gly Lys Leu Cys Leu Ala Cys Val Lys Ser
                65                  70                  75

Gly Asp Glu Thr Arg Leu Gln Leu Glu Ala Val Asn Ile Thr Asp
                80                  85                  90

Leu Ser Lys Asn Lys Asp Gln Asp Lys Arg Phe Thr Phe Ile Leu
```

-continued

```
                 95                  100                 105
Ser Asp Ser Gly Pro Thr Thr Ser Phe Glu Ser Ala Ala Cys Pro
                110                 115                 120

Gly Trp Phe Leu Cys Thr Ala Leu Glu Ala Asp Arg Pro Val Ser
                125                 130                 135

Leu Thr Asn Arg Pro Glu Glu Ala Met Met Val Thr Lys Phe Tyr
                140                 145                 150

Phe Gln Lys Glu
            154
```

(2) INFORMATION FOR SEQ ID NO:6:

(i) SEQUENCE CHARACTERISTICS:
        (A) LENGTH:33 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:6:

CCCTCTGGGA GAAAATCCAG CAAGATGCAA GCC                      33

(2) INFORMATION FOR SEQ ID NO:7:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:7:

CTACTCGTCC TCCTGGAAGT AGAA                                24

(2) INFORMATION FOR SEQ ID NO:8:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:8:

GTAAAACGAC GGCCAGT                                          17

(2) INFORMATION FOR SEQ ID NO:9:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE:oligonucleotide (xi) SEQUENCE DESCRIPTION: SEQ ID NO:9:

AACAGCTATG ACCATG                                            16

(2) INFORMATION FOR SEQ ID NO:10:

(i) SEQUENCE CHARACTERISTICS:
        (A) LENGTH: 23 basepairs
        (B) TYPE: nucleic acid

```
        (C) STRANDEDNESS: single
        (D) TOPOLOGY: linear (ii) MOLECULE TYPE: oligonucleotide (xi) SEQUENCE DESCRIPTION: SEQ ID NO:10:

CAGCCTCGGT GGGGTGGACC CTC                                              23

(2) INFORMATION FOR SEQ ID NO:11:

(i) SEQUENCE CHARACTERISTICS:
        (A) LENGTH: 23 base pairs
        (B) TYPE: nucleic acid
        (B) STRANDEDNESS: single
        (D) TOPOLOGY: linear (ii) MOLECULE TYPE: oligonucleotide (xi) SEQUENCE DESCRIPTION: SEQ ID NO:11:

TTGATGGGAG AGTGGGGGGA GGA                                              23

(2) INFORMATION FOR SEQ ID NO:12:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:12:

TCTGGGATGT TAACCAGAAG ACCT                                             24

(2) INFORMATION FOR SEQ ID NO:13:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:13:

ACTCAACACA TACAACACAC ATTC                                             24

(2) INFORMATION FOR SEQ ID NO:14:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:14:

CTCAGACAGT GGCCCCACCA CCAG                                             24

(2) INFORMATION FOR SEQ ID NO:15:

(i) SEQUENCE CHARACTERISTICS:
        (A) LENGTH: 24 basepairs
        (B) TYPE: nucleic acid
        (C) STRANDEDNESS: single
        (D) TOPOLOGY: linear (ii) MOLECULE TYPE: oligonucleotide
```

(xi) SEQUENCE DESCRIPTION: SEQ ID NO:15:

TTCATTCAGC TCCGGGGTAC CGAG                                               24

(2) INFORMATION FOR SEQ ID NO:16:

(i) SEQUENCE CHARACTERISTICS:
        (A) LENGTH: 24 basepairs
        (B) TYPE: nucleic acid
        (C) STRANDEDNESS: single
        (D) TOPOLOGY: linear (ii) MOLECULE TYPE:oligonucleotide (xi) SEQUENCE DESCRIPTION: SEQ ID NO:16:

GAGATGAGAC CAGGCTCCAG CTGG                                               24

(2) INFORMATION FOR SEQ ID NO:17:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:17:

GCCGACCGGC CTGTCAGCCT CACC                                               24

(2) INFORMATION FOR SEQ ID NO:18:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:18:

GAGAGATCTT GCCGTCCCTT GGGGAAGAGA CCTTG                                   35

(2) INFORMATION FOR SEQ ID NO:19:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:19:

GGGGGGGAAT TCCGGAATGG ACACACTATT ATT                                     33

(2) INFORMATION FOR SEQ ID NO:20:

(i) SEQUENCE CHARACTERISTICS:
        (A) LENGTH: 177 amino acids
        (B) TYPE: amino acid
        (C) STRANDEDNESS: single
        (D) TOPOLOGY: linear (ii) MOLECULE TYPE: human IL-1ra sequence (xi) SEQUENCE DESCRIPTION: SEQ ID NO: 20:

Met Glu Ile Cys Arg Gly Leu Arg Ser His Leu Ile Thr Leu Leu
1               5                   10                  15

-continued

```
Leu Phe Leu Phe His Ser Glu Thr Ile Cys Arg Pro Ser Gly Arg
            20                  25                  30

Lys Ser Ser Lys Met Gln Ala Phe Arg Ile Trp Asp Val Asn Gln
            35                  40                  45

Lys Thr Phe Tyr Leu Arg Asn Asn Gln Leu Val Ala Gly Tyr Leu
            50                  55                  60

Gln Gly Pro Asn Val Asn Leu Glu Glu Lys Ile Asp Val Val Pro
            65                  70                  75

Ile Glu Pro His Ala Leu Phe Leu Gly Ile His Gly Gly Lys Met
            80                  85                  90

Cys Leu Ser Cys Val Lys Ser Gly Asp Glu Thr Arg Leu Gln Leu
            95                 100                 105

Glu Ala Val Asn Ile Thr Asp Leu Ser Glu Asn Arg Lys Gln Asp
           110                 115                 120

Lys Arg Phe Ala Phe Ile Arg Ser Asp Ser Gly Pro Thr Thr Ser
           125                 130                 135

Phe Glu Ser Ala Ala Cys Pro Gly Trp Phe Leu Cys Thr Ala Met
           140                 145                 150

Glu Ala Asp Gln Pro Val Ser Leu Thr Asn Met Pro Asp Glu Gly
           155                 160                 165

Val Met Val Thr Lys Phe Tyr Phe Gln Glu Asp Glu
           170                 175     177
```

(2) INFORMATION FOR SEQ ID NO:21:

(i) SEQUENCE CHARACTERISTICS:
        (A) LENGTH: 178 amino acids
        (B) TYPE: amino acid
        (C) STRANDEDNESS: single
        (D) TOPOLOGY: linear (ii) MOLECULE TYPE: mouse IL-1ra sequence (xi) SEQUENCE DESCRIPTION: SEQ ID NO:21:

```
Met Glu Ile Cys Trp Gly Pro Tyr Ser His Leu Ile Ser Leu Leu
1                5                  10                  15

Leu Ile Leu Leu Phe His Ser Glu Ala Ala Cys Arg Pro Ser Gly
            20                  25                  30

Lys Arg Pro Cys Lys Met Gln Ala Phe Arg Ile Trp Asp Thr Asn
            35                  40                  45

Gln Lys Thr Phe Tyr Leu Arg Asn Asn Gln Leu Ile Ala Gly Tyr
            50                  55                  60

Leu Gln Gly Pro Asn Ile Lys Leu Glu Gly Lys Ile Asp Met Val
            65                  70                  75

Pro Ile Asp Leu His Ser Val Phe Leu Gly Ile His Gly Gly Lys
            80                  85                  90

Leu Cys Leu Ser Cys Ala Lys Ser Gly Asp Asp Ile Lys Leu Gln
            95                 100                 105

Leu Glu Glu Val Asn Ile Thr Asp Leu Ser Lys Asn Lys Glu Glu
           110                 115                 120

Asp Lys Arg Phe Thr Phe Ile Arg Ser Glu Lys Gly Pro Thr Thr
           125                 130                 135

Ser Phe Glu Ser Ala Ala Cys Pro Gly Trp Phe Leu Cys Thr Thr
           140                 145                 150

Leu Glu Ala Asp Arg Pro Val Ser Leu Thr Asn Thr Pro Glu Glu
           155                 160                 165

Pro Leu Ile Val Thr Lys Phe Tyr Phe Gln Glu Asp Gln
           170                 175
```

```
                  170             175        178
```

(2) INFORMATION FOR SEQ ID NO:22:

(i) SEQUENCE CHARACTERISTICS:
        (A) LENGTH: 177 amino acids
        (B) TYPE: amino acid
        (C) STRANDEDNESS: single
        (D) TOPOLOGY: linear (ii) MOLECULE TYPE: rabbit IL-1ra sequence (xi) SEQUENCE DESCRIPTION: SEQ ID NO:22:

```
Met Arg Pro Ser Arg Ser Thr Arg Arg His Leu Ile Ser Leu Leu
1               5                   10                  15

Leu Phe Leu Phe His Ser Glu Thr Ala Cys Arg Pro Ser Gly Lys
                20                  25                  30

Arg Pro Cys Arg Met Gln Ala Phe Arg Ile Trp Asp Val Asn Gln
                35                  40                  45

Lys Thr Phe Tyr Leu Arg Asn Asn Gln Leu Val Ala Gly Tyr Leu
                50                  55                  60

Gln Gly Pro Asn Ala Lys Leu Glu Glu Arg Ile Asp Val Val Pro
                65                  70                  75

Leu Glu Pro Gln Leu Leu Phe Leu Gly Ile Gln Arg Gly Lys Leu
                80                  85                  90

Cys Leu Ser Cys Val Lys Ser Gly Asp Lys Met Lys Leu His Leu
                95                  100                 105

Glu Ala Val Asn Ile Thr Asp Leu Gly Lys Asn Lys Glu Gln Asp
                110                 115                 120

Lys Arg Phe Thr Phe Ile Arg Ser Asn Ser Gly Pro Thr Thr Thr
                125                 130                 135

Phe Glu Ser Ala Ser Cys Pro Gly Trp Phe Leu Cys Thr Ala Leu
                140                 145                 150

Glu Ala Asp Gln Pro Val Ser Leu Thr Asn Thr Pro Asp Asp Ser
                155                 160                 165

Ile Val Val Thr Lys Phe Tyr Phe Gln Glu Asp Gln
                170                 175    177
```

(2) INFORMATION FOR SEQ ID NO:23:

(i) SEQUENCE CHARACTERISTICS:
        (A) LENGTH: 178 amino acids
        (B) TYPE: amino acid
        (C) STRANDEDNESS: single
        (D) TOPOLOGY: linear (ii) MOLECULE TYPE: rat IL-1ra sequence (xi) SEQUENCE DESCRIPTION: SEQ ID NO:23:

```
Met Glu Ile Cys Arg Gly Pro Tyr Ser His Leu Ile Ser Leu Leu
1               5                   10                  15

Leu Ile Leu Leu Phe Arg Ser Glu Ser Ala Gly His Pro Ala Gly
                20                  25                  30

Lys Arg Pro Cys Lys Met Gln Ala Phe Arg Ile Trp Asp Thr Asn
                35                  40                  45

Gln Lys Thr Phe Tyr Leu Arg Asn Asn Gln Leu Ile Ala Gly Tyr
                50                  55                  60

Leu Gln Gly Pro Asn Thr Lys Leu Glu Glu Lys Ile Asp Met Val
                65                  70                  75

Pro Ile Asp Phe Arg Asn Val Phe Leu Gly Ile His Gly Gly Lys
```

```
                 80                  85                  90
Leu Cys Leu Ser Cys Val Lys Ser Gly Asp Asp Thr Lys Leu Gln
             95                 100                 105
Leu Glu Glu Val Asn Ile Thr Asp Leu Asn Lys Asn Lys Glu Glu
            110                 115                 120
Asp Lys Arg Phe Thr Phe Ile Arg Ser Glu Thr Gly Pro Thr Thr
            125                 130                 135
Ser Phe Glu Ser Leu Ala Cys Pro Gly Trp Phe Leu Cys Thr Thr
            140                 145                 150
Leu Glu Ala Asp His Pro Val Ser Leu Thr Asn Thr Pro Lys Glu
            155                 160                 165
Pro Cys Thr Val Thr Lys Phe Tyr Phe Gln Glu Asp Gln
            170                 175         178
```

(2) INFORMATION FOR SEQ ID NO:24:

(i) SEQUENCE CHARACTERISTICS:
        (A) LENGTH: 534 base pairs
        (B) TYPE: nucleic acid
        (C) STRANDEDNESS: single
        (D) TOPOLOGY: linear (ii) MOLECULE TYPE: human IL-1ra DNA sequence (xi) SEQUENCE DESCRIPTION: SEQ ID NO:24:

```
ATGGAAATCT  GCAGAGGCCT  CCGCAGTCAC  CTAATCACTC                    40
TCCTCCTCTT  CCTGTTCCAT  TCAGAGACGA  TCTGCCGACC                    80
CTCTGGGAGA  AAATCCAGCA  AGATGCAAGC  CTTCAGAATC                   120
TGGGATGTTA  ACCAGAAGAC  CTTCTATCTG  AGGAACAACC                   160
AACTAGTTGC  TGGATACTTG  CAAGGACCAA  ATGTCAATTT                   200
AGAAGAAAAG  ATAGATGTGG  TACCCATTGA  GCCTCATGCT                   240
CTGTTCTTGG  GAATCCATGG  AGGGAAGATG  TGCCTGTCCT                   280
GTGTCAAGTC  TGGTGATGAG  ACCAGACTCC  AGCTGGAGGC                   320
AGTTAACATC  ACTGACCTGA  GCGAGAACAG  AAAGCAGGAC                   360
AAGCGCTTCG  CCTTCATCCG  CTCAGACAGT  GGCCCCACCA                   400
CCAGTTTTGA  GTCTGCCGCC  TGCCCCGGTT  GGTTCCTCTG                   440
CACAGCGATG  GAAGCTGACC  AGCCCGTCAG  CCTCACCAAT                   480
ATGCCTGACG  AAGGCGTCAT  GGTCACCAAA  TTCTACTTCC                   520
AGGAGGACGA  GTAG                                                 534
```

(2) INFORMATION FOR SEQ ID NO:25:

(i) SEQUENCE CHARACTERISTICS:
        (A) LENGTH: 537 base pairs
        (B) TYPE: nucleic acid
        (C) STRANDEDNESS: single
        (D) TOPOLOGY: linear (ii) MOLECULE TYPE: mouse IL-1ra DNA sequence (xi) SEQUENCE DESCRIPTION: SEQ ID NO:25:

```
ATGGAAATCT  GCTGGGGACC  CTACAGTCAC  CTAATCTCTC                    40
TCCTTCTCAT  CCTTCTGTTT  CATTCAGAGG  CAGCCTGCCG                    80
CCCTTCTGGG  AAAAGACCCT  GCAAGATGCA  AGCCTTCAGA                   120
```

-continued

| | | | | |
|---|---|---|---|---|
| ATCTGGGATA | CTAACCAGAA | GACCTTTTAC | CTGAGAAACA | 160 |
| ACCAGCTCAT | TGCTGGGTAC | TTACAAGGAC | CAAATATCAA | 200 |
| ACTAGAAGAA | AAGATAGACA | TGGTGCCTAT | TGACCTTCAT | 240 |
| AGTGTGTTCT | TGGGCATCCA | CGGGGGCAAG | CTGTGCCTGT | 280 |
| CTTGTGCCAA | GTCTGGAGAT | GATATCAAGC | TCCAGCTGGA | 320 |
| GGAAGTTAAC | ATCACTGATC | TGAGCAAGAA | CAAAGAAGAA | 360 |
| GACAAGCGCT | TTACCTTCAT | CCGCTCTGAG | AAAGGCCCCA | 400 |
| CCACCAGCTT | TGAGTCAGCT | GCCTGTCCAG | GATGGTTCCT | 440 |
| CTGCACAACA | CTAGAGGCTG | ACCGTCCTGT | GAGCCTCACC | 480 |
| AACACACCGG | AAGAGCCCCT | TATAGTCACG | AAGTTCTACT | 520 |
| TCCAGGAAGA | CCAATAG | | | 537 |

(2) INFORMATION FOR SEQ ID NO:26:

(i) SEQUENCE CHARACTERISTICS:
        (A) LENGTH: 534 base pairs
        (B) TYPE: nucleic acid
        (C) STRANDEDNESS: single
        (D) TOPOLOGY: linear (ii) MOLECULE TYPE: rabbit IL-1ra DNA sequence (xi) SEQUENCE DESCRIPTION: SEQ ID NO:26:

| | | | | |
|---|---|---|---|---|
| ATGAGACCCT | CCAGGAGCAC | CCGCAGGCAC | CTAATCTCCC | 40 |
| TCCTCCTCTT | CCTGTTCCAT | TCAGAGACAG | CCTGCCGCCC | 80 |
| TTCTGGGAAA | AGACCTTGCA | GGATGCAGGC | CTTCAGAATC | 120 |
| TGGGATGTTA | ACCAGAAGAC | CTTCTACTTG | AGAAACAACC | 160 |
| AACTAGTCGC | TGGTTACTTG | CAAGGCCCAA | ATGCCAAATT | 200 |
| AGAAGAAAGG | ATAGATGTGG | TGCCCCTTGA | GCCTCAGCTC | 240 |
| CTGTTCCTGG | GCATCCAGAG | GGGGAAGTTG | TGCCTGTCTT | 280 |
| GTGTGAAGTC | TGGGGATAAG | ATGAAGCTCC | ATTTGGAGGC | 320 |
| CGTTAACATC | ACTGACCTGG | GCAAGAACAA | GGAGCAGGAC | 360 |
| AAGCGCTTCA | CCTTCATCCG | CTCCAATAGT | GGCCCTACCA | 400 |
| CCACCTTCGA | GTCTGCCTCC | TGCCCGGGCT | GGTTTCTCTG | 440 |
| CACGGCCCTG | GAGGCTGACC | AGCCGGTCAG | CCTCACCAAC | 480 |
| ACCCCGGACG | ACTCCATCGT | GGTCACCAAG | TTCTACTTCC | 520 |
| AGGAGGACCA | GTAG | | | 534 |

(2) INFORMATION FOR SEQ ID NO:27:

(i) SEQUENCE CHARACTERISTICS:
        (A) LENGTH: 537 base pairs
        (B) TYPE: nucleic acid
        (C) STRANDEDNESS: single
        (D) TOPOLOGY: linear (ii) MOLECULE TYPE: rat IL-1ra DNA sequence (xi) SEQUENCE DESCRIPTION: SEQ ID NO:27:

| | | | | |
|---|---|---|---|---|
| ATGGAAATCT | GCAGGGGACC | TTACAGTCAC | CTAATCTCTC | 40 |
| TCCTTCTCAT | CCTTCTGTTT | CGTTCAGAGT | CAGCTGGCCA | 80 |

-continued

| | | | | |
|---|---|---|---|---|
| CCCTGCTGGG | AAAAGACCCT | GCAAGATGCA | AGCCTTCAGA | 120 |
| ATCTGGGATA | CTAACCAGAA | GACCTTCTAC | CTGAGGAACA | 160 |
| ACCAGCTCAT | TGCTGGGTAC | TTACAAGGAC | CAAATACCAA | 200 |
| ACTAGAAGAA | AAGATAGACA | TGGTGCCTAT | TGACTTTCGG | 240 |
| AATGTGTTCT | TGGGCATCCA | CGGGGGCAAG | CTGTGCCTGT | 280 |
| CTTGTGTCAA | GTCTGGAGAT | GACACCAAGC | TCCAGCTGGA | 320 |
| GGAGGTTAAC | ATCACTGATC | TGAACAAGAA | CAAAGAAGAA | 360 |
| GACAAGCGCT | TTACCTTCAT | CCGCTCCGAG | ACAGGCCCTA | 400 |
| CCACCAGCTT | CGAATCACTT | GCCTGTCCAG | GATGGTTCCT | 440 |
| CTGCACAACA | CTAGAGGCTG | ATCATCCCGT | GAGCCTCACC | 480 |
| AACACACCAA | AAGAGCCCTG | TACAGTCACA | AAGTTCTACT | 520 |
| TCCAGGAAGA | CCAATAG | | | 537 |

All prior art papers disclosed herein are hereby incorporated by reference. Modifications and other embodiments of the invention will be apparent to those skilled in the art to which this invention relates having the benefit of the foregoing teachings, descriptions, and associated drawings. The present invention is therefore not to be limited to the specific embodiments disclosed but is to include modifications and other embodiments which are within the scope of the appended claims.

What is claimed is:

1. A substantially pure and homogeneous soluble protein comprising the amino acid sequence of canine IL-1ra selected from the group consisting of SEQ ID NO 3, SEQ ID NO 4, and SEQ ID NO 5.

* * * * *

UNITED STATES PATENT AND TRADEMARK OFFICE
CERTIFICATE OF CORRECTION

PATENT NO : 6,018,029
DATED : January 25, 2000
INVENTOR(S): Gerald M. Fuller, et al.

It is certified that error appears in the above-identified patent and that said Letters Patent are hereby corrected as shown below:

Title page, beginning at line 1, change title to read --
PROTEIN SEQUENCE ENCODING CANINE INTERLEUKIN-1 RECEPTOR ANTAGONIST--.

Column 1, Line 1, please delete "DNA" and replace with
-- PROTEIN SEQUENCE--.

Signed and Sealed this

First Day of May, 2001

Attest:

NICHOLAS P. GODICI

Attesting Officer    Acting Director of the United States Patent and Trademark Office